United States Patent [19]

Kuhlman

[11] Patent Number: 4,679,255
[45] Date of Patent: Jul. 14, 1987

[54] WELDER'S MASK WITH REMOTE CONTROLLED EYE SHIELD

[76] Inventor: Thomas E. Kuhlman, R. R. 7748, Spirit Lake, Iowa 51360

[21] Appl. No.: 837,030

[22] Filed: Mar. 6, 1986

[51] Int. Cl.⁴ ............................................. A61F 9/06
[52] U.S. Cl. ......................................................... 2/8
[58] Field of Search .................... 2/8, 432, 424, 6, 10, 2/9; 219/147

[56] References Cited

U.S. PATENT DOCUMENTS

| | | | |
|---|---|---|---|
| 3,096,430 | 7/1963 | Farr | 2/8 X |
| 3,368,220 | 2/1968 | Wenzel | 2/8 |
| 3,943,573 | 3/1976 | Budmiger | 2/8 |
| 4,011,594 | 3/1977 | Gilbaud et al. | 2/8 |
| 4,101,979 | 7/1978 | Tarrone | 2/8 |
| 4,109,132 | 8/1978 | Butoi | 2/8 X |
| 4,293,757 | 10/1981 | Niemi | 2/8 X |
| 4,418,267 | 11/1983 | Pfanzelt | 2/8 X |
| 4,510,625 | 4/1985 | Mizuki | 2/8 |
| 4,546,498 | 10/1985 | Fantin | 2/8 X |

FOREIGN PATENT DOCUMENTS 2034171 6/1980 United Kingdom ........................ 2/8

*Primary Examiner*—Peter Nerbun
*Attorney, Agent, or Firm*—Zarley, McKee, Thomte, Voorhees & Sease

[57] ABSTRACT

A welder's mask having a remote controlled eye shield for allowing the user to remotely and independently control opening of the eye shield when not needed, and closing of the eye shield when needed, which includes a conventional welder's mask housing having a viewing opening means to mount the mask housing upon the user's head. A conventional welder's eye shield is adjustably secured to the mask housing in such a way that it is moveable between a closed position covering the viewing opening, and an open position uncovering the viewing opening. A motor means, mounted on the mask housing, has a connecting means between the motor means and the eye shield which transmits the output of the motor means to the eye shield to move it between the open and closed positions. An independent remote control radio transmitter means has a control switch means which, when operated, sends appropriate radio signals to a radio receiving means which receives and converts the radio signals into electrical signals which are transferred to instruct the motor means to move the eye shield between the opened and closed positions, according to desire. The motor means and transmitter means are operatively connectable to a first power means which can be secured to the mask housing. The transmitter means is operatively connected to a second power means for its independent and remote operation.

8 Claims, 4 Drawing Figures

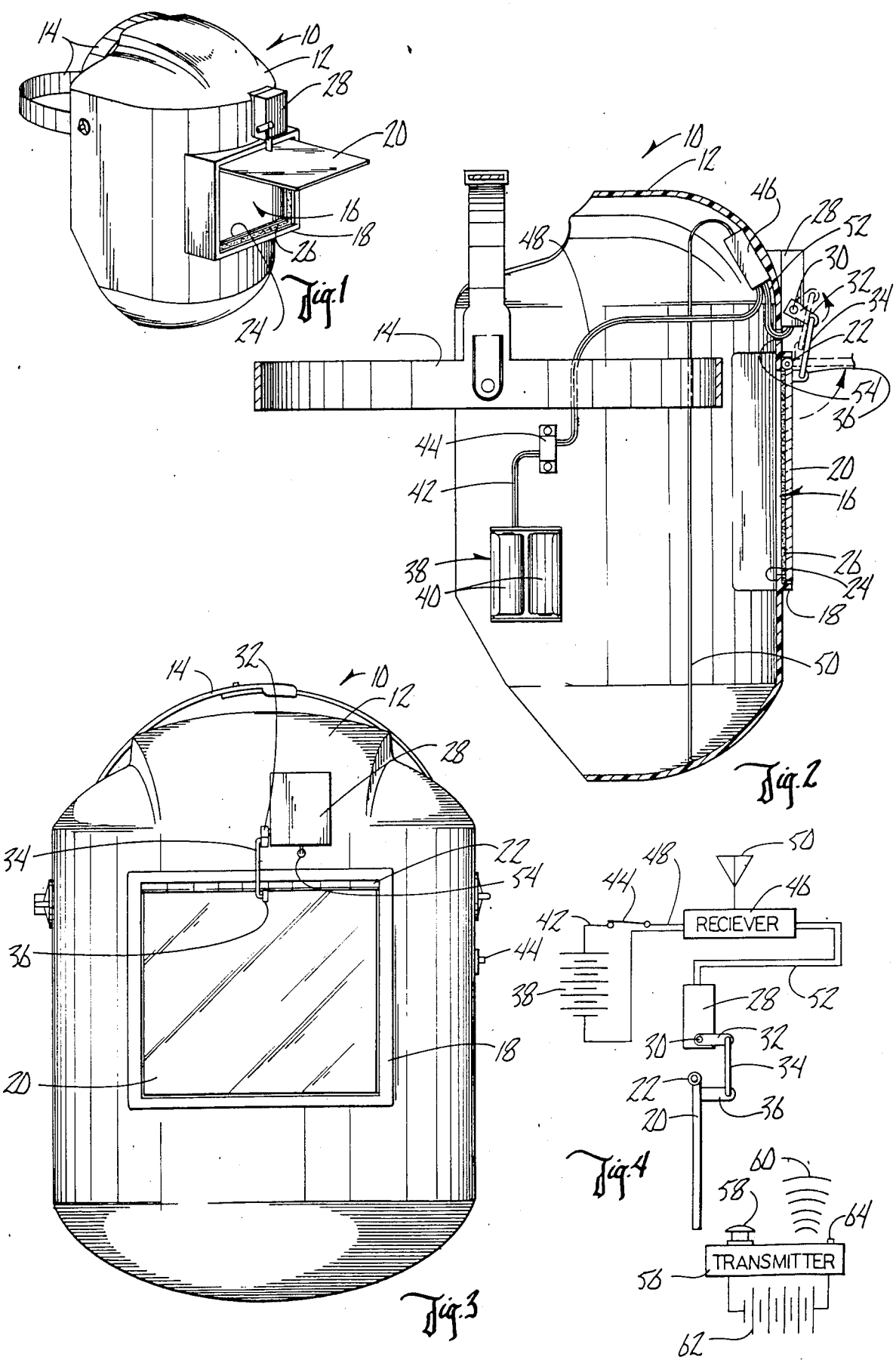

WELDER'S MASK WITH REMOTE CONTROLLED EYE SHIELD

BACKGROUND OF THE INVENTION

1. Field of the Invention

This invention relates to a welder's mask having a remote controlled eye shield, and more particularly, to a welder's mask having a protective eye shield which can be opened or closed according to remote radio control.

2. Problems In The Art

Conventional arc welding requires, at the same time, vision by the welder of the workpiece and welding equipment at the welding point and protection of the welder's eyes from the high intensity welding arc. Additionally, protection of the welder's face is needed from the heat and particles involved in the welding process.

Conventional welding masks or helmets utilize a protective housing which covers the front of the user's face and include a darkly tinted window or eye shield through which the welder can view the welding without harm to the welder's eyes. Because of the darkness of the tint needed to protect against the high intensity welding arc, the welder cannot adequately see either the workpiece, the welding instruments, or the welding controls with the eye shield in place if the welding arc is not operating. Originally, the welder therefore had to many times remove and replace the entire welder's mask during welding which was cumbersome, time consuming, and wearing.

Welders many times use protective gloves and clothing which reduces agility and ability to easily remove, replace, or adjust the mask. An improvement was developed by decreasing the weight of the mask using materials of sufficient protective properties but of significantly less weight, and by incorporating a mounting means for the user's head which allowed pivoting of the mask upwardly and downwardly from the user's face. This eliminated the need to remove and replace the mask each time the welder needed to view the workpiece independent of the eye shield.

However, this system is still cumbersome, time consuming, and wearisome for the welder. This is especially true in a production line setting where workpiece after workpiece is moved in front of the welder and repetitive welding is done on successive workpieces.

Another attempt at improving over conventional welder's masks included utilizing a moveable eye shield which is moved by a motor connected to a control cord which the welder operates to close or open the eye shield. Still further, another device utilizes a photoelectric eye associated with workpieces which are successively moved into place to raise and lower the eye shield for repetitive welding.

The remote control cord proved to be cumbersome, easily entangled, and many times may interfere with the welding procedure. It does not allow movement of the welder away from the control or the mask and is subject to damage in the heat and procedure of welding. The photoelectric eye device is limited to control by the workpieces and does not allow the welder independent and needed flexibility of control. Furthermore, such a system is imprecise in that the need to open or close the eye shield is more dependent upon the need for unobstructed vision by the welder, rather than timing of the workpiece or other stimuli. Also, the photoelectric eye is subject to other non-welding related obstructions and can become blocked, clogged or otherwise have operating deficiencies in the welding environment.

It is therefore the primary object of the present invention to provide a welder's mask having a remote controlled eye shield which improves over and solves the problems in the art.

A further object of the invention is to provide a welder's mask having a remote controlled eye shield which allows the user to have independence and complete control of opening and closing the eye shield.

A further object of the invention is to provide a welder's mask having a remote controlled eye shield which moves the eye shield out of the viewing opening of the mask to allow unobstructed vision of the welder without any requirement of moving or adjusting the welder's mask.

Another object of the invention is to provide a welder's mask having a remote controlled eye shield which does not have any cords or other physical structure connected between the welder's mask and the controls for opening and closing the eye shield.

A further object of the invention is to provide a welder's mask having a remote controlled eye shield which is light weight, easy to operate, durable, and economical.

These and other objects, features, and advantages of the invention will become apparent with reference to the accompanying specification and claims.

SUMMARY OF THE INVENTION

This invention utilizes a conventional welder's mask and eye shield with the eye shield being adjustably secured to the mask housing so that it can be either closed over the viewing opening or removed from the viewing opening to alternatively protect the welder's eyes or allow for unobstructed vision by the welder.

Operation of closing and opening the eye shield is accomplished by mounting a small motor means, a radio signal receiver, and a power supply on the mask housing itself, the motor means being in operative connection with the eye shield. A radio signal transmitter having a manually operated control switch means is then used to transmit radio signals corresponding to the user's desire to either open or close the eye shield.

The remote, independent, radio signal transmitter allows the user to, by choice, close or open the eye shield according to desire by operation of the control switch means on the transmitter. The mask does not have to be manually hinged upward, lifted, or removed to move the deeply tinted eye shield from the line of vision of the welder, nor does the mask have to be manually replaced when the eye shield is needed for the user's protection. The above steps are eliminated thus saving time, energy and effort, and increasing efficiency and ease of operation.

BRIEF DESCRIPTION OF THE DRAWINGS

FIG. 1 is a perspective view of the invention.

FIG. 2 is a side sectional elevational view of the invention.

FIG. 3 is a front elevational view of the invention.

FIG. 4 is a schematic view of the operational circuitry and components of the invention.

DETAILED DESCRIPTION OF THE PREFERRED EMBODIMENT

In reference to the drawings, and particularly FIG. 1, a preferred embodiment of the present invention is illustrated and will now be explained. A welder's mask 10 is shown including a mask housing 12 which serves to cover most of the front of the face and head of the user and some of the front of the neck of the user. The mask 10 is mounted to the user's head by mounting straps 14 which are adjustable for different sized heads and are conventionally secured to mask housing 12.

A viewing opening 16 exists in the front of mask housing 12 and is positioned to be in alignment with the user's eyes when mask 10 is positioned on the user's head. In the preferred embodiment as shown in FIG. 1, it can be seen that viewing opening 16 is defined by an eye shield framework 18 which presents a planar frame for the planar eye shield 20, as opposed to the curved surface of mask housing 12.

Eye shield 20 is made of a deeply tinted glass or similar material such as is known in the art. Eye shield 20 must be deeply tinted to protect the user's eyes from the high intensity light of the arc of the welding apparatus. Out of necessity, eye shield 20 must be so deeply tinted that without the high intensity arc being in operation, the user cannot see well enough to position the welding instruments with relation to the welding spot. It is for this reason that conventional welder's masks must be constantly removed or adjusted out of the vision of the welder between welding operations.

In the preferred embodiment shown in the drawings, eye shield 20 is hingeably attached to mask housing 12 by hinge 22 (see FIGS. 2 and 3). Eye shield 20 is moveable into mateable abutment with the inside ridges 24 of eye shield framework 18. Additionally, a gasket 26 is interposed between ridges 24 and eye shield 20 to further insure that when eye shield 20 is closed in eye shield framework 18, an effective seal is formed so that light and particles cannot pass into the interior of mask housing 12.

A small motor 28 is secured to the outside of mask housing 12 above eye shield framework 18 and has a drive shaft 30 extending laterally out of one side of the motor 28. A first arm 32 is rigidly attached at one end to drive shaft 30. A second arm 34 is attached at one end to the upper part of eye shield 20 and extends perpendicularly outward therefrom.

A linkage piece 36 is hingeably secured to the outer ends of first and second arms 32 and 34. It can therefore be seen that rotation of drive shaft 30 in a counterclockwise direction causes first arm 32 to raise and therefore linkage piece 36 and second arm 34 cause eye shield 20 to hinge upwardly away from viewing opening 16. Conversely, clockwise rotation of drive shaft 30 causes first arm 32 to rotate downwardly and the weight of eye shield 20 and transmitted force through linkage piece 36 and second arm 34 cause eye shield 20 to rotate about hinge 22 downwardly into sealing abutment in eye shield framework 18.

By referring to FIG. 2, the operation of first and second arms 32 and 34, linkage piece 36 and eye shield 20 can be seen. FIG. 2 shows eye shield 20 in what will be called the closed position whereas the phantom lines show eye shield 20 in what will be called its open or raised position. Also, phantom lines show the different positions of first and second arms 32 and 34 and linkage piece 36.

FIG. 2 also shows the operating circuitry secured to mask housing 12. A power supply 38, which is composed of batteries 40, is secured to the inside of mask housing 12. Electrical wires 42 are connected to a switch 44 also secured to mask housing 12. Switch 44 extends through mask housing 12 so that it can be operated exteriorly as shown in FIG. 3. A radio signal receiver 46 is also secured to the inside of mask housing 12 and is connected to switch 44 by electrical wires 48. An antenna 50 for receiver 46 is mounted along the inside of mask housing 12. Radio signal receiver 46 is in turn connected by electrical wires 52 to motor 28 through an aperture 54 in mask housing 12.

It can thus be seen that most of the circuitry is contained within housing 12 thereby protecting it from damage by the welding procedure or otherwise. Motor 28 and receiver 46 operate on DC current as supplied by batteries 40. Operation and connection of this circuitry is conventional in the art.

FIG. 4 shows a head-on view of welder's mask 10 with eye shield 20 in the closed position. It can be seen that welder's mask 10 of the present invention supplies the same amount of protection to the user as do conventional welder's masks.

FIG. 4 depicts schematically the basic operational circuitry and elements of the invention. Switch 44, receiver 46, and motor 28 are all electrically connected to batteries 40 and operate on the same circuit. Switch 44 enables operation of receiver 46 and motor 28 when in a closed or "on" position. When opened or turned "off", switch 44 preserves batteries 40 and does not allow operation of the circuitry thus saving power in batteries 40. It will be noted that eye shield 20 and the connecting elements to motor 28 (first and second arms 32 and 34 and linkage piece 36) are also schematically depicted in FIG. 4.

A radio signal transmitter 56 is the final element utilized in operation of the invention 10. By utilizing a control switch 58, the user can send radio signals (represented by curved lines 60) which are received by antenna 50 of receiver 46 when turned "on". Receiver 46 then converts radio signals 60 to an electrical signal which is passed through wires 52 to instruct motor 28 to operate drive shaft 30 in the desired direction to open or close eye shield 20. Transmitter 56 is likewise powered by batteries 62 and can be turned "on" or "off" by a switch 64.

Mask housing 12, mounting straps 14, and eye shield 20 are conventional elements and can be obtained through manufacturers or vendors of welding equipment.

In the preferred embodiment, radio signal transmitter 56 and radio signal receiver 46 are conventional, known-in-the-art elements which are obtainable from vendors dealing in radio transmitters and receivers. Specifically, these elements in the preferred embodiment were taken from a radio controlled model car sold at Radio Shack ® stores. Motor 28 is simply a small servo motor which was also taken from the radio controlled car. The motor 28 rotates drive shaft 30 in either the clockwise or counterclockwise direction according to the radio signal transmitted by radio signal transmitter 56. Receiver 46 differentiates between the signals sent by transmitter 56 and converts that into the appropriate electrical signal to operate motor 28 in the correct direction.

Operation of the invention 10 is as follows. During welding operation, the user, for safety of the user's eyes and protection of the user's face, positions the mask housing 12 upon the user's head and over the user's face. Eye shield 20 would be seated in eye shield framework 18 completely sealing off any light or particles from the user's face, except light passing through eye shield 20. As can be seen in FIG. 3. in this position, welder's mask 10 functions as a conventional welding mask.

When however, the welding prooedure is done, the extreme dark tint of eye shield 20 prevents adequate vision for the user and therefore eye shield 20 must be removed from the line of sight of the user for the user to adequately see. Assuming that switches 44 and 64 are turned "on", control switch 58 of transmitter 56 is then operated accordingly to transmit a radio signal. Receiver 46 picks up the signal through antenna 50 and converts and transmits the radio signal into an electrical signal to motor 28 to turn drive shaft 30 counterclockwise which raises eye shield 20. This allows the user to view through viewing opening 16 without the obstruction of eye shield 20.

Operating control switch 58 in the reverse direction causes eye shield 20 to be closed by reversing the operation of motor 28. Thus, control of eye shield 20 is completely remote and by radio signal, without any cords or manual adjustments to the mask itself being required.

Of course, both switch 44 on mask housing 12, and the transmitter 56 must be turned on to allow the respective circuitries to operate.

It will be appreciated that the present invention can take many forms and embodiments. The true essence and spirit of this invention are defined in the appended claims, and it is not intended that the embodiment of the invention presented herein should limit the scope thereof.

For example, instead of eye shield 20 being hingeably attached to mask housing 12, it could slide within rails or otherwise accomplish the same result. Motor 28 could operate a small gear system to slide eye shield 20 between a closed and opened position.

As another alternative, different types of linkages between motor 28 and eye shield 20 could be utilized. Further, eye shield 20 might be spring loaded. Motor 28 and linkage piece 36 with arms 32 and 34 might function to hold eye shield 20 and eye shield framework 18 in a closed position but then simply release it when the user desires eye shield 20 to be opened.

Many different types of radio transmitters and receivers could be utilized as could different types of portable power supplies and circuitries.

Also, it is to be pointed out that while transmitter 56 could be operated manually by the user, either as a separate small control box or incorporated into the welding apparatus control panel, it could also be operated in the form of a foot switch. Still further, it could be operated automatically by an external stimuli. For instance, if welding is taking place along an assembly line with workpieces continuously moving into position for the welding procedure, the transmitter switch could be activated by each workpiece as it comes into position to close eye shield 20 and then as it moves away to open eye shield 20.

Other embellishments and variations obvious to one skilled in the art are included within the invention defined by the claims and are not described herein.

What is claimed is:

1. A welder's mask having a remote controlled eye shield comprising:

a mask housing having a viewing opening and means for mounting the mask housing upon the head of a user;

a welder's eye shield having an upper edge portion hingedably secured to the mask housing and being hingeably movable between a closed position covering the viewing opening and an open position uncovering the viewing opening in the mask housing;

motor means having a drive shaft and being mounted on the mask housing and being operably connectable to a first battery power source mounted on the mask housing, the motor means having connecting linkage means attached between the eye shield and the motor means, the drive shaft of the motor means being operable in first and second directions to move the connecting linkage means to correspondingly move the eye shield to any resting position between and including the open and the closed positions;

the connecting means comprising a first arm rigidly secured at a first end to the drive shaft of the motor means, a second arm rigidly secured at a first end to and extending from the eye shield, and a linkage arm hingeably secured between the second ends of the first and second arms;

remote control radio signal transmitter means operably connectable to a second battery power source and having control switch means for transmitting a radio signal corresponding to moving the eye shield between the opened position and the closed position; and radio signal receiving means operably connectable to the first battery power means and the motor means for receiving and transferring the radio signal to the motor means.

2. The device of claim 1 wherein the radio transmitter means comprises means to emit at least two different radio signals, one corresponding to opening the eye shield, the other corresponding to closing the eye shield.

3. The device of claim 2 wherein the radio receiving means has means for converting the first and second signals of the remote control radio transmitter means appropriately to instruct the motor means to move the eye shield to an open position or a closed position according to operation of the control switch means.

4. The device of claim 4 further comprising a power switch means operatively connected to at least the first power source to turn the first power source on or off.

5. The device of claim 1 further comprising a power switch means operatively connected to at least the second power source to turn the second power source on or off.

6. The device of claim 1 wherein the control switch means of the remote control radio transmitter means is a foot switch.

7. A welder's mask having a remote controlled eye shield comprising:

a mask housing having a viewing opening and means for mounting the mask housing upon the head of a user;

an eye shield hingeably secured to the mask housing and movable to any resting position between and including a closed position covering the viewing opening and an open position uncovering the viewing opening in the mask housing;

gasket means positioned around the viewing opening to provide a seal between the mask housing and eye shield when the eye shield is moved to a closed position;

motor means mounted on the mask housing and being operably connectable to a battery power means;

connecting linkage means operably connected between the motor means and the eye shield;

radio signal receiving means operatively connected to said battery power means and to the motor means;

remote control radio signal transmitter means operatively connectable to a battery power source and having a control switch means having a first position causing the transmitter to send an eye shield open signal and a second position causing the transmitter to send an eye shield close signal; and the motor means moving the eye shield to a closed position when the eye shield close signal is transmitted by the transmitter, and moving the eye shield to an open position when the eye shield open signal is transmitted by the transmitter.

8. The welder's mask of claim 7 wherein until said transmitter discontinues transmitting, said motor means will continue to exert force on said eye shield, even when said eye shield has reached said open or closed positions, so that complete opening of said eye shield can be achieved in the open position and complete sealing closure can be achieved in the closed position.

* * * * *